United States Patent
Knebel et al.

(10) Patent No.: US 7,683,216 B2
(45) Date of Patent: Mar. 23, 2010

(54) CONTINUOUS PROCESS FOR THE PREPARATION OF ALKYLENEIMINES

(75) Inventors: Thomas Knebel, Schifferstadt (DE); Gerd Saas, Einselthum (DE); Wolfgang Schreieck, Ludwigshafen (DE); Horst Schroeder, Bad Duerkheim (DE); Manfred Winter, Dittelsheim-Hessloch (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/105,663

(22) Filed: Apr. 18, 2008

(65) Prior Publication Data

US 2008/0262265 A1 Oct. 23, 2008

(30) Foreign Application Priority Data

Apr. 20, 2007 (EP) .................................. 07106615

(51) Int. Cl.
*C07C 209/68* (2006.01)
(52) U.S. Cl. ......................................... 564/445; 564/448
(58) Field of Classification Search ........................ None
See application file for complete search history.

(56) References Cited

FOREIGN PATENT DOCUMENTS

| | | |
|---|---|---|
| DE | 195 48 317 A1 | 6/1997 |
| EP | 0 227 461 B1 | 7/1987 |
| EP | 0 228 898 B1 | 7/1987 |
| EP | 0 230 776 B1 | 8/1987 |
| JP | 5-10593 | 1/1993 |
| WO | WO 96/22975 | 8/1996 |

OTHER PUBLICATIONS

Henry Wenker, "The Preparation of Ethylene Imine from Monoethanolamine", Journal of the American Chemical Society, vol. 57, 1935, p. 2328.

*Primary Examiner*—Brian J Davis
(74) *Attorney, Agent, or Firm*—Oblon, Spivak, McClelland, Maier & Neustadt, L.L.P.

(57) ABSTRACT

A process for the preparation of alkyleneimines by subjecting sulfuric acid monoesters of aminoalkanols to an at least two-stage reaction with aqueous bases at a temperature of at least 110° C. under pressure, relieving the pressure of the reaction mixture and distilling off the alkyleneimines from the reaction mixture after each reaction stage, wherein the conversion in the first stage is from 40 to 90% and that in the second stage is from more than 90% to 99.99%.

19 Claims, No Drawings

CONTINUOUS PROCESS FOR THE PREPARATION OF ALKYLENEIMINES

The invention relates to a process for the preparation of alkyleneimines by subjecting sulfuric acid monoesters of aminoalkanols to an at least two-stage reaction with aqueous bases at a temperature of at least 110° C. under pressure, relieving the pressure of the reaction mixture and distilling off the alkyleneimines from the reaction mixture after each reaction stage.

Ethyleneimine is prepared, for example, by the Wenker process by reacting 2-aminoethyl hydrogen sulfate with aqueous sodium hydroxide solution at a temperature of at least 160° C. under pressure, relieving the pressure of the reaction mixture and distilling off the ethyleneimine, cf. H. Wenker, Journal of the American Chemical Society, Vol. 57, 2328 (1935). The yields of ethyleneimine, based on the 2-aminoethyl hydrogen sulfate used, are in need of improvement.

DE-A 195 48 317 discloses a process for the preparation of ethyleneimine by reacting, for example, 2-aminoethyl hydrogen sulfate with aqueous alkali metal and/or alkaline earth metal bases at temperatures of from 80 to 280° C. and pressures up to 100 bar, the reaction being carried out in a reactor cascade consisting of at least two reactors connected in series, in such a way that the conversion of 2-aminoethyl hydrogen sulfate in each reactor of the cascade is from 20 to 90% and that the ethyleneimine is distilled off from the reaction mixture after each pass through a reactor of the cascade. The pressure of the reaction mixture is first relieved, a part of the ethyleneimine distilling off. Energy is then supplied to the reaction mixture for substantially removing the ethyleneimine, for example by electrical heating or by heating with a natural gas burner or by passing in steam. The energy balance of the process is, however, unfavorable.

Ethyleneimine can also be prepared by dehydration of ethanolamine in the gas phase over various catalysts. Thus, for example, JP-B 50/10593 discloses the use of catalysts comprising tungsten oxide and oxides of Li, Mg, Ni, Mo, Bi, Sn, Si or Al for this purpose. According to WO 89/05797, molecular sieves comprising aluminum silicates, aluminum phosphates or silicon aluminum phosphates are used in the dehydration of ethanolamine in the gas phase. Other catalysts for intramolecular elimination of water from alkanolamines in the gas phase are oxide materials which comprise silicon or phosphorus in bound form as substantial constituents, cf. EP-B 0 227 461, EP-B 0 228 898 and EP-B 0 230 776.

WO 96/22975 discloses the preparation of ethyleneimine by dehydration of ethanolamine in the gas phase at temperatures of at least 250° C. over solid catalysts in a fluidized bed under reduced pressure, a part of the solid catalyst being removed from the reactor while maintaining the fluidized bed and being regenerated and then recycled to the reactor.

In the abovementioned process for the dehydration of 2-aminoethanol, both the yield of ethyleneimine and the on-stream times of the catalysts are unsatisfactory.

It is the object of the invention to improve the energy balance and the yield in the preparation of alkyleneimines by reacting sulfuric acid monoesters of aminoalkanols with aqueous bases at a temperature of at least 110° C. under pressure, relieving the pressure of the reaction mixture and distilling off the ethyleneimine.

The object is achieved, according to the invention, by a process for the preparation of alkyleneimines by subjecting sulfuric acid monoesters of aminoalkanols to an at least two-stage reaction with aqueous bases at a temperature of at least 110° C. under pressure, relieving the pressure of the reaction mixture and distilling off the alkyleneimines from the reaction mixture after each reaction stage, the conversion in the first stage being from 40 to 90% and that in the second stage being from more than 90% to 99.99%.

Aminoalkanols can be characterized, for example, with the aid of the following formula:

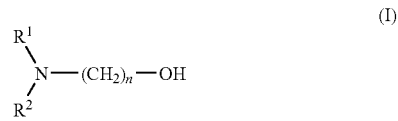

in which the substituents $R^1$ and $R^2$ are identical or different and are hydrogen, aliphatic substituents which may be straight-chain, branched and/or cyclic and have 1 to 10 carbon atoms, substituted aliphatic radicals whose substituents are inert under the reaction conditions, and heterocycloaliphatic radicals having 3 to 6 carbon atoms, and n is from 2 to 10, preferably from 1 to 4, particularly preferably n is 2. 2-Aminoethanol (monoethanolamine) is particularly preferred, i.e. in formula I $R^1$, $R^2$ are each hydrogen and n is 2. Compounds of the formula I in which $R^1$ is H and $R^2$ is methyl or ethyl are furthermore preferred.

A particularly preferred alkyleneimine is ethyleneimine, which is prepared by reacting 2-aminoethyl hydrogen sulfate with at least one aqueous base. The molar ratio of sulfuric acid monoesters of aminoalkanols to base is, for example, from 1:1 to 1:5, preferably from 1:1.1 to 1:2 and is generally in the range from 1:1.2 to 1:1.9. The reaction is carried out in an aqueous medium. The concentration of the sodium salt of sulfuric acid monoesters of aminoalcohols in the reaction solution is, for example, from 5 to 30% by weight, preferably from 10 to 25% by weight.

Suitable bases are, for example, alkali metal and alkaline earth metal hydroxides. Sodium hydroxide solution or potassium hydroxide solution, is preferably used, in particular sodium hydroxide solution.

The reaction temperature is at least 110° C. It is generally in the range from 140 to 250° C. and is preferably from 160 to 210° C. To carry out the reaction, it is advantageous to heat the reaction mixture as rapidly as possible to the temperature required for the reaction. Apparatuses having as small a volume (hold-up) as possible and a large internal surface area are therefore preferably used for this purpose. For example, spiral heat exchangers or plate-type heat exchangers are particularly suitable. The reaction is preferably carried out continuously under pressure. The pressures are, for example, at least 3 bar and are generally in the range from 2 to 120 bar, preferably from 5 to 100 bar.

In order to bring the reaction mixture particularly rapidly to the required reaction temperature, steam is preferably passed—likewise under pressure—directly into the aqueous reaction mixture. Depending on the level of the pressure chosen in each case during the reaction, the reaction mixture is present as a single phase, i.e. only in the liquid phase, or as two phases (liquid and gaseous phase). The one-phase procedure is preferred here because oscillations which arise on introduction of the steam into the reaction mixture are substantially avoided thereby. The heating of the reaction mixture should last for not more than 25%, preferably not more than 20%, of the total reaction time in the first reaction stage.

The mixture which is heated to the reaction temperature and, in the case of the preparation of ethyleneimine, substantially comprises an aqueous mixture of 2-aminoethanol hydrogen sulfate and aqueous sodium hydroxide solution is then passed through a reactor in which the conversion to alkyleneimine, preferably ethyleneimine, takes place. In the first stage of the reaction, the conversion is taken to a conversion of not more than 95%. The conversion of the first stage is generally from 20 to 90% and is preferably from 60 to 85%. In general, the reaction is carried out in such a way that the conversion in the first stage is from 40 to 90% and that in the second stage is up to 99.99%, i.e. the conversion in the second stage is virtually complete. In the case of a two-stage reaction procedure, the sulfuric acid monoesters of aminoalkanols are converted in the first stage preferably to an extent of from 60 to 85% and, after the alkyleneimine formed has been distilled off, the unconverted sulfuric acid monoester is converted virtually completely in the second stage into alkyleneimine and alkali metal sulfate.

At a reaction temperature of 200° C., the residence time in this reaction stage is, for example, from 5 to 250 seconds, preferably from 20 to 50 seconds. In this stage of the process, too, the reaction is preferably carried out continuously. It is preferably effected in a tubular reactor. The reactors preferred for the reaction are designed so that the reaction mixture therein can be passed through continuously with plug flow. Such reactors have only little back-mixing. These reactors are primarily tubular reactors which may be helical or in the form of a spiral. However, the reaction mixture may also be discharged in pulses, i.e. batchwise, from the reactor.

After leaving the reactor, the reaction mixture is preferably let down into a column which is operated under atmospheric pressure. It is fed, for example, into the upper third of the column. In the column, the separation of the alkyleneimine, preferably of the ethyleneimine, from the reaction mixture takes place. The alkyleneimine is removed at the top of the column and condensed. The distillation is generally carried out in such a way that, for example, a 40 to 70% strength by weight aqueous solution of the alkyleneimine results. In the preferred embodiment of the process, the distillation is effected continuously. In principle, the alkyleneimine is removed from the reaction mixture after each reaction stage at the top of the column with the aid of a column under atmospheric pressure, and the product obtained in the stripping section of the column (for example, dividing wall column or column with liquid side take-off) or in the bottom of the column is fed to a further stage for the further reaction of the sulfuric acid monoester.

The bottom product which comprises virtually no ethyleneimine is discharged at the bottom of the column. The quantity of heat required for operating the column is supplied to the system at the bottom of the column by a heat exchanger. Since the conversion of the sulfuric acid monoester or aminoalcohols in the first stage is carried out at most to 95%, preferably from 40 to 90%, the further reaction of the bottom product separated off with the aid of the column is effected in at least one further stage, which may be followed by an additional stage or 2, 3 or 4 further stages. The bottom product separated off in the column is then pumped via a heat exchanger into a second reactor, which is likewise designed to be pressure-tight. Here too, steam is preferably passed under pressure into the reaction mixture in order to heat it as rapidly as possible to the reaction temperature. The reaction mixture then enters a second reactor whose construction substantially corresponds to the first reactor. It is preferably likewise a tubular reactor which, however, may have different dimensions so that, on continuous operation, a longer residence time of the reaction mixture than in the first reactor can be established therein. The residence time of the reaction mixture in the second reactor is preferably at least twice as long as in the first reactor.

If the second reaction stage is not followed by any further reaction stages, the conversion of the salt of the sulfuric acid monoester of aminoalcohols is continued until it is up to 99.99%, i.e. the conversion is virtually complete. The reaction mixture emerging from the second reactor is preferably removed continuously and let down into a column in which alkyleneimine, preferably ethyleneimine, is distilled off via the top.

The distillation process corresponds substantially to the above-described operation of the column in which the reaction mixture from the first reactor is distilled. However, in the two-stage procedure described here, the bottom of the column no longer comprises any salts of sulfuric acid monoesters of aminoalcohols because they were virtually completely cleaved in the second stage. The bottom product which is removed from the column after the second reaction stage is disposed of. It mainly comprises an alkyleneimine-free aqueous solution of alkali metal sulfate, excess base, preferably sodium hydroxide solution, and unidentified organic by-products.

Compared with the process for the cleavage of the esters in only one stage, the multistage cleavage according to the invention of the sulfuric acid monoesters of alkanolamines has the advantage that 8 to 10% higher yields, based on the ester used, are obtained and that lower costs are incurred for disposing of the waste.

In a particularly preferred embodiment of the process according to the invention, two reactors connected in series are operated continuously in an integrated heat system and a dividing wall column is operated for working up the two reactor discharges. The heat exchange is preferably effected countercurrently but may also be carried out with cross-flow or cocurrently. The reactors are primarily the pressure-tight, tubular apparatuses described above. The reaction mixture which leaves the first reactor is preferably passed through a heat exchanger in which, preferably countercurrently under pressure, it heats a freshly fed aqueous reaction solution of the sodium salt of 2-aminoethyl hydrogen sulfate and excess sodium hydroxide solution to a temperature of, for example, from 140 to 180° C., before it is let down to atmospheric pressure in a column equipped with a dividing wall, in which ethyleneimine is distilled via the top from the reaction mixture.

The fresh reaction solution heated to 140 to 180° C. under pressure in the first heat exchanger is heated to the reaction temperature, which is preferably from 190 to 210° C., before entry into the reactor by passing in superheated steam. After passing through the first reactor in which the sulfuric acid monoester undergoes, for example, from 40 to 90% cleavage, the reaction mixture continuously enters the first heat exchanger in which freshly fed in reaction solution is heated.

The bottom product which is taken off in the lower third of the dividing wall column is virtually free of ethyleneimine. It is passed under pressure through a second heat exchanger in which it is heated countercurrently to 140 to 180° C. by the reaction product which leaves the second reactor and is then further heated to 190 to 210° C. by passing in superheated steam under pressure. It then passes through the second reactor and thereafter the second heat exchanger and is then let down to atmospheric pressure in the other chamber of the dividing wall column. Ethyleneimine is distilled off via the top of the column. The energy is supplied at the bottom of the column by a heat exchanger or by directly feeding in steam.

At the bottom of the column, an aqueous solution which comprises sodium sulfate, excess sodium hydroxide solution and organic by-products is removed. The yield is at least 80%, based on the salt of the sulfuric acid monoester used.

The alkyleneimines, in particular ethyleneimine, are used for the preparation of polymers. Polyethyleneimine can be used, for example, for imparting wet strength to paper and as a retention aid and drainage aid in the production of paper and in adhesives.

We claim:

1. A process for preparing at least one alkyleneimine, comprising:
   a first heating of a mixture comprising at least one sulfuric acid monoester of aminoalkanol and at least one aqueous base to a temperature of at least 100° C.;
   a first reacting of said at least one sulfuric acid monoester of aminoalkanol and said at least one aqueous base which is carried out at said temperature and at a pressure of at least 3 bar to form said at least one alkyleneimine;
   a first depressurizing of said mixture;
   a first separating of said at least one alkyleneimine from said mixture;
   a second reacting of said at least one sulfuric acid monoester of aminoalkanol and said at least one aqueous base at said temperature and at a pressure of at least 3 bar to form said at least one alkyleneimine;
   a second depressurizing of said mixture; and
   a second separating of said at least one alkyleneimine from said mixture, wherein
   i) said first heating is carried out for no longer than 25% of the total time of said first reacting,
   ii) from 40 to 90% of said at least one sulfuric acid monoester of aminoalkanol present in said mixture is converted to said at least one alkyleneimine during said first reacting; and
   iii) from 90 to 99.99% of said at least one sulfuric acid monoester of aminoalkanol present in said mixture is converted to said at least one alkyleneimine during said second reacting.

2. The process according to claim 1, wherein
said at least one sulfuric acid monoester of aminoalkanol is 2-aminoethyl hydrogen sulfate; and
said at least one alkylenimine is ethyleneimine.

3. The process according to claim 1 or 2, wherein
from 60 to 85% of said at least one sulfuric acid monoester of aminoalkanol present in said mixture is converted to said at least one alkyleneimine during said first reacting; and
up to 99.99% of said at least one sulfuric acid monoester of aminoalkanol present in said mixture is converted to said at least one alkyleneimine during said second reacting.

4. The process according to claim 1, wherein said process is carried out continuously.

5. The process according to claim 1, wherein said process is carried out in a tubular reactor.

6. The process according to claim 5, wherein the said process is effected with plug flow.

7. The process according to claim 1, wherein said heating is carried out by contacting said mixture with superheated steam prior to said first reacting.

8. The process according to claim 1,
further comprising passing said mixture through a heat exchanger prior to said first or second reacting.

9. The process according to claim 1, wherein
said first reacting takes place in a first reactor;
said second reacting takes place in a second reactor; and
a residence time of said mixture in said second reactor is at least twice as long as a residence time of said mixture in said first reactor.

10. The process according to claim 1, further comprising:
passing said mixture upon carrying out said first reacting in a first reactor through a heat exchanger;
feeding an aqueous reaction solution comprising a sodium salt of at least one sulfuric acid monoester of aminoalkanol and excess base through said heat exchanger to heat said aqueous reaction solution to a temperature of from 140 to 180° C. prior to said first depressurizing to admix said aqueous reaction solution with said mixture;
depressurizing said mixture obtained from said feeding in a column having a dividing wall; and separating said at least one alkyleneimine from a top of said column.

11. The process according to claim 1, wherein at least one of said first reacting and said second reacting is carried out at a temperature of from 140 to 250° C.

12. The process according to claim 1, wherein at least one of said first reacting and said second reacting is carried out at a temperature of from 160 to 210° C.

13. The process according to claim 1, wherein at least one of said first reacting and said second reacting is carried out at a pressure of from 3 to 120 bar.

14. The process according to claim 1, wherein at least one of said first reacting and said second reacting is carried out at a pressure of from 5 to 100 bar.

15. The process according to claim 1, wherein said first heating is carried out for no longer than 20% of the total time of said first reacting.

16. The process according to claim 1, wherein said at least one aminoalkanol is represented by formula (I)

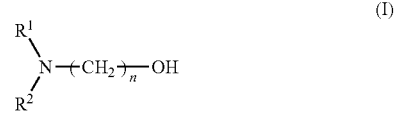

wherein
each of $R^1$ and $R^2$, independently, represents a hydrogen atom; a straight-chain, branched or cyclic $C_1$-$C_{10}$ aliphatic radical; a substituted aliphatic radical where the substituent is inert during said process; or a $C_3$-$C_6$ heterocycloaliphatic radical, and
n represents an integer of from 2 to 10.

17. The process according to claim 16, wherein $R^1$ is a hydrogen atom and $R^2$ a methyl or ethyl radical.

18. The process according to claim 1, wherein a molar ratio of said at least one sulfuric acid monoester of aminoalkanol to said at least one aqueous base is from 1:1 to 1:5.

19. The process according to claim 1, wherein a molar ratio of said at least one sulfuric acid monoester of aminoalkanol to said at least one aqueous base is from 1:1.1 to 1:2.

* * * * *